US006338943B1

(12) United States Patent
Houthoff et al.

(10) Patent No.: US 6,338,943 B1
(45) Date of Patent: Jan. 15, 2002

(54) METHODS FOR LABELING NUCLEOTIDES, LABELED NUCLEOTIDES AND USEFUL INTERMEDIATES

(75) Inventors: Hendrick Jan Houthoff, Amsterdam; Jan Reedijk, Leiden; Tinka Jelsma, Almere; Robert Jochem Heetebrij, Utrecht; Herman Hendricus Volkers, Monnickendam, all of (NL)

(73) Assignee: Kreatech Biotechnology B.V., Amsterdam (NL)

( * ) Notice: Subject to any disclaimer, the term of this patent is extended or adjusted under 35 U.S.C. 154(b) by 0 days.

(21) Appl. No.: 09/402,707

(22) PCT Filed: Oct. 8, 1997

(86) PCT No.: PCT/NL97/00559

§ 371 Date: Oct. 8, 1999

§ 102(e) Date: Oct. 8, 1999

(87) PCT Pub. No.: WO98/15564

PCT Pub. Date: Apr. 16, 1998

(30) Foreign Application Priority Data

Oct. 8, 1996 (EP) .............................................. 96202792

(51) Int. Cl.[7] .......................... C12Q 1/68; C12P 19/34; G01N 33/00; C07H 21/62; C07H 21/04
(52) U.S. Cl. ........................ 435/6; 435/91.1; 435/91.2; 436/501; 436/94; 436/172; 436/800; 530/350; 536/23.1; 536/24.3; 536/25.3

(58) Field of Search .......................... 435/6, 91.1, 91.2, 435/183; 436/501, 94, 800, 172; 536/23.1, 24.3, 25.3; 530/350

(56) References Cited

FOREIGN PATENT DOCUMENTS

| EP | 0 282 672 A1 | * | 9/1988 |
| GB | 2 148 891 A | * | 6/1985 |
| WO | WO 9201699 A1 | * | 2/1992 |
| WO | WO 9635696 A1 | * | 11/1996 |

* cited by examiner

Primary Examiner—Bradley L. Sisson
(74) Attorney, Agent, or Firm—Hoffmann & Baron, LLP

(57) ABSTRACT

The present invention provides improved methods for labeling nucleotides. The method of the invention for labeling nucleotides comprises the steps of: reacting a reactive moiety of a linker, which linker is a platinum compound having a stabilizing bridge and two reactive moieties, with an electron donating moiety of a spacer, which spacer comprises a chain having at least four atoms and at least one heteroatom in the chain, which spacer further comprises said electron donating moiety at one end of the chain and a reactive moiety at the other end of the chain; reacting the reactive moiety of said spacer with a label; reacting the other reactive moiety of said linker with a nucleotide. A major advantage of the invention is that all nucleotides can be labeled by the method of the invention, whereas until now the attachment of a label was mostly restricted to one or certain nucleotides.

28 Claims, No Drawings

METHODS FOR LABELING NUCLEOTIDES, LABELED NUCLEOTIDES AND USEFUL INTERMEDIATES

The invention relates to methods for labeling nucleotides using linkers (linking moieties between labels and bioorganic molecules, which linkers are based on platinum compounds).

Platinum (coordination) compounds have been considered interesting molecules for a very long time. For a review of these compounds and their uses we refer to Reedijk et al. (Structure and Bonding 67, p.53–89, 1987). Especially Cisplatinum has received a lot of attention as a possible anti-tumour drug. This anti-tumour reactivity of platinum compounds originates from their having at least two reactive groups (preferably cis-oriented towards each other), which make it possible to cross-link DNA molecules, thereby inhibiting the replication of these DNA molecules.

The British patent application 2 148 891 discloses cis-platinum complexes, which are six-coordinated. The platinum is attached to two halogens or hydroxy groups, two additional halogens and to an ethylenediamine derived group, such as 1,2-diamino-2-methylpropane or 1,2-diamino-2-methylbutane. The complexes are said to have an excellent anti-tumor effect.

In the European patent application four-coordinated complexes of platinum to 2,3-alkyl-1,4-butanediamine and two halogens are described for their anti-tumor effect.

Different four-coordinated platinum complexes are described in the European patent application 0 386 243. The complexes comprise a diamine bidentate ligand and two 2-arylalkanoic acid or 3-aryl-2-oxoalkanoic acid ligands. These complexes are stated to have a strong growth inhibiting action on certain leukemia cells and are used for their oncostatic activity.

U.S. Pat. No. 4,207,416 discloses ethylenediamine-platinum(II) 2,4-dioxopyrimidine complexes as having a high anti-tumor activity and low mammalian toxicity.

A different use of platinum (coordination) compounds has been disclosed in PCT application (WO92/01699) wherein a platinum compound having only two reactive moieties (denominated as leaving groups therein) is reacted with a fluorescein to obtain a labeled platinum compound which can bind (non-covalently) to a nucleic acid, preferably at the N-7 position of a guanine residue.

Several methods for labeling nucleotides have been described in the literature. For a long time, the standard method has been to use radioactive isotope labeling. However, there are a number of problems associated with the use of radioisotopes, such as potential health hazards, disposal problems and instability problems.

In order to overcome these problems, Dale et al., Biochemistry, 14, (1975), 2447–2457, have proposed to use direct covalent mercuration as a labeling technique for nucleotides and polynucleotides. It was found, that cytosine and uracil may be mercurated at their C5-position under mild conditions. Further, Gebeyehu et al., Nucleic Acids Research, 15, (1987), 4513–4534, have reported that adenine and cytosine may be labeled with biotin derivatives through an aliphatic linker of from 3 to 17 atoms.

A major drawback of these known methods is that they are not suitable for labeling all different nucleotides. For instance, Dale et al. reported that their covalent mercuration method leads to negative results for adenine, thymine and guanine bases. In some cases, for example when only a few residues of a certain nucleotide are present in a certain nucleic acid or when the terminating nucleotide residue of a nucleic acid has to be labeled, it is desired to have at one's disposal a method for labeling any nucleotide residue.

The present invention provides such a method. The method for labeling nucleotides of the invention comprises the steps of:
reacting a reactive moiety of a linker of the formula

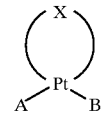

(I)

wherein X represents any stabilizing bridge and wherein A and B represent the same or different reactive moieties, with an electron donating moiety of a spacer, which spacer comprises a chain having at least four atoms and at least one heteroatom in the chain, which spacer further comprises said electron donating moiety at one end of the chain and a reactive moiety at the other end of the chain;
reacting the reactive moiety of said spacer with a label;
reacting the other reactive moiety of said linker with a nucleotide.

According to the invention, the linker may first be attached to the nucleotide and then to the spacer, or vice versa and the spacer may first be coupled to the label and then to the linker or vice versa.

The reactive moiety of the spacer may be any reactive moiety that will enable the reaction between the spacer and the label in such a manner that a labeling moiety comprising a label and a spacer is formed, which labeling moiety is sufficiently stable.

The main purpose for labeling nucleotides is that these labeled nucleotides can be incorporated in nucleic acid molecules. Modified nucleotides, especially those wherein a (bulky) label is attached to the nucleotide, are often built-in into nucleic acids with a much lower efficiency. The methods according to the invention result in labeled nucleotides which are built-in into nucleic acids with a higher efficiency than the labeled nucleotides available to date. This is probably due to the selection of the spacers according to the invention in combination with the platinum-based linkers according to the invention.

The label to be used according to the invention is not critical. In principle all labels which can be attached to a nucleotide and are employed to date can be used. These labels may be radioactive labels, enzymes (which need reaction with a substrate to be detected), specific binding pairs components such as avidin, streptavidin or biotin, biocytin, iminobiotin, colloidal dye substances, fluorochromes (rhodamin, etc.), reducing substances (eosin, erythrosin, etc.), (coloured) latex sols, digoxigenin, metals (ruthenium), metal sols or other particulate sols (selenium, carbon and the like), dansyl lysin, Infra Red Dyes, coumarines (amino methyl coumarine), antibodies, protein A, protein G, etc. The invention has most benefits with bulkier labels such as biotin, avidin, streptavidin, digoxygenin or a functional equivalent thereof.

The invention is not limited to nucleotides or nucleosides as such; derivatives and functional equivalents are also included. The usual nucleotides adenine, thymidine, cytosine, guanine and uridine are preferred. Especially the purines are preferred which have a very good incorporation rate.

For coupling of the spacer to the platinum linker an electron donating moiety is required. In a preferred method the electron donating moiety is an amine or a thiolate anion, which have both proven to be very succesful. It was found that aromatic amines, such as imidazoles or purines, are capable of forming very strong bonds to platinum and thus are very suitable for use as the electron donating moiety.

The spacer is an important aspect of the present invention; it provides the easiest coupling between label and linker. For avoiding steric hindrance in incorporation of the nucleotide into the nucleic acid it should at least be four atoms long, preferably it is at least four carbon atoms long and has at least one heteroatom in that carbon chain. A heteroatom confers a certain amount of rigidity on the spacer. This rigidity provides an additional assurance that steric factors will not obstruct a convenient linking of a nucleotide and a label. It is preferred that at least one heteroatom is an oxygen atom, which positively effects the hydrophilicity of the spacer.

Preferably, the spacer comprises no more than 20 carbon atoms in the chain, which is preferably an essentially non-branched chain, thus causing no steric hindrance. The reason for this will be clear.

A highly preferred spacer is 1,8-diamino-3,6-dioxaoctane, herein referred to as Dadoo. Dadoo is a very flexible compound with a distal primary amine group and a size that makes it very suitable for use as spacer according to the invention.

Another highly preferred spacer of the invention is an oligolysine or a polylysine. Due to their structure and conformation, these molecules create the most convenient environment for an optimal interaction among the actual label, the nucleotide and the platinum. An additional advantage of the use of lysine chains as the spacer is, that by altering the number of lysine units in the chain, the optimal conditions for specific labels and nucleotides or nucleic acids can be attained. Given a certain application, the skilled person will easily determine how many lysine units are required for optimum results.

An especially interesting labeling moiety comprising a label and a spacer, has the formula

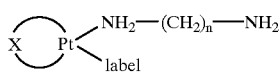

(II)

or the formula

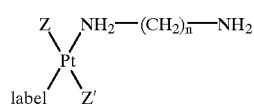

(III)

wherein X represents any stabilizing bridge, Z and Z' represent a non-leaving ligand and n is an integer of from 2 to 10.

Accordingly, the linker-spacer-label-system, or labeling substance, with the labeling moiety of formula (II) or formula (III) has the formula

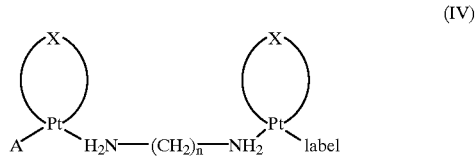

(IV)

or the formula

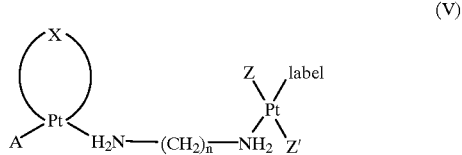

(V)

wherein A, X, Z, Z' and n have the above meanings.

The non-leaving ligands Z and/or Z' are preferably an $NH_3$, $NH_2R$, $NHR_2$ or $NR_3$ group, wherein R represents an alkyl group having from 1 to 6 carbon atoms, because these ligands have an even smaller leaving-group character than other non-leaving ligands.

The interesting feature of using the labeling moieties having formulas (II) and (III) is that both the nucleotide and the actual label have the benefit of being bonded directly to a platinum atom, while at the same time these moieties are sufficiently far apart to avoid steric hindrance.

The linkers according to the invention preferably are platinum compounds wherein X represents an aliphatic diamine. In a preferred embodiment of the invention, one or both of the nitrogen atoms of the aliphatic diamine are shielded. A suitable manner of shielding these nitrogen atoms consists of substitution with one or two alkyl groups of from 1 to 6 carbon atoms, preferably methyl groups. This is advantageous in that hydrogen bonding between the triphosphate group of a nucleotide and the stabilizing bridge is prevented. Preferably, a diamine having 2–6 carbon atoms is used, most preferably an ethylene diamine group, which is well-known for its stabilizing effect on this class of platinum compounds. In this case, the linker has the formula

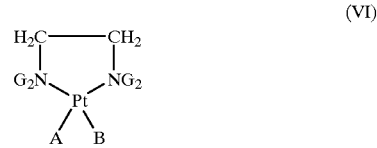

(VI)

wherein G represents hydrogen or an alkyl group of from 1 to 6 carbon atoms and A and B represent the same or different reactive moieties.

The coupling or reactive moieties A and B are preferably the same and selected from the group consisting of $NO_3^-$, $SO_3^-$, $Cl^{31}$, $I^-$, or other halogens.

The invention of course also encompasses a labeled nucleotide obtainable by a method as disclosed above.

In addition, the invention encompasses a labeling substance for labeling nucleotides by a method as disclosed above. The labeling substance of the invention has the formula

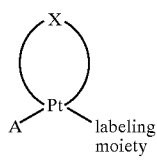

(VII)

wherein X and A have the above meanings and the labeling moiety comprises a label and a spacer as described above. Of course the labeling substances of the invention can also be used for labeling purposes other than labeling nucleotides. It was found that numerous (bio-) organic compounds, i.e. nearly every bio-organic molecule which contains an accessible sulphur or nitrogen atom, for example proteins, can be labeled with the platinum compounds of the invention.

A great advantage of the invention arises from the use of the platinum compounds having formula (I) as linkers in the methods of preparing labeled nucleotides according to the invention. These linkers can be prepared by very convenient and reliable methods.

In WO92/01699 the starting compounds disclosed for preparing labeled platinum compounds are platinum(II) (ethylenediamine)dichloride and platinum(II) (ethylenediamine)(Me$_2$SO)Cl. The first one can be obtained commercially, the second one (the preferred one) must be synthesized. In the dichloride compound, the Cl-ions are less readily substituted by a label or a nucleotide, respectively. In the latter case, the total nucleotide labeling time will be appreciably longer, up to several hours, instead of several minutes.

The methods for preparing the linkers that are used in the method of labeling nucleotides according to the invention are based on the selection of suitable starting compounds of the formula PtE$_4$ wherein E is an electronegative group, preferably a halogen or NO$_3^-$ or SO$_3^-$. The reaction, which is described in the examples, of these starting compounds with e.g. ethylenediamine is very simple and efficient. Moreover, this reaction leads to very suitable symmetric intermediate compounds for producing labeled nucleotides. A major advantage of using these compounds is that when a stabilizing bridge for the resulting platinum compound has to be attached that no blocking reagents have to be employed. Another advantage is that the resulting intermediate compounds can again be labeled without the use of blocking agents. Therefore steps removing blocking agents can be eliminated completely. Furthermore the yields of these reactions are very high. Yet another advantage of the use of these symmetrical starting compounds is that no mixtures of different resulting compounds can be formed, which may interfere with the following reaction and reduce yield or require extra separation steps.

A very suitable intermediate compound according to the invention is platinum(II)(ethylenediamine)(NO$_3$)$_2$. This substance can very easily be provided with a suitable spacer and a labeling group, resulting in labeling substances which can, through substitution of the remaining NO$_3$-group be linked to a nucleotide quite easily. Furthermore the methods for producing these compounds and the resulting compounds do not involve highly toxic substances such as DMSO.

The intermediate compounds can be labeled with any suitable label (also known as marker) through a spacer as disclosed hereinabove.

Furthermore, the known advantages (from WO92/01699 for instance) are of course also obtained with the present methods and compounds. Another advantage of the platinum compounds is that they can be detected more or less directly by using the platinum as a nucleus for depositing silver or other metal crystals.

By binding the labeling substance to a nucleotide residue, DNA or RNA molecules, be it single stranded or otherwise, can be easily detected, but it also allows for the production of probes for hybridization techniques wherein unlabeled DNA/RNA molecules hybridize to the labeled probe. The platinum linker labeled nucleotides hardly interfere with the hybridization, if at all. Also, this technique obviates the use of modified nucleotides in preparing probes.

Nucleotides modified in accordance with the practices of this invention and oligo- and polynucleotides into which the modified nucleotides have been incorporated or oligo- and polynucleotides that have been directly modified using these novel platinum compounds may be used as probes in biomedical research, clinical diagnostics and recombinant DNA technology.

Other advantages and embodiments of the invention will become clear from the following experimental part and the examples.

Experimental

Synthesis of Intermediate Platinum Compounds

These compounds, i.e. the linkers having formula (I), may be prepared by a process which involves:

(a) reacting a compound having the structure:

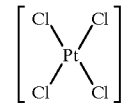

with KI in a suitable solvent under suitable conditions so as to form a iodated platinum compound having the structure:

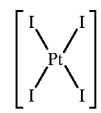

(b) reacting said iodated platinum compound with ethylenediamine in a suitable solvent so as to form a diethyleneamine iodated platinum compound and represented by the formula Pt(en)I$_2$ and having the structure:

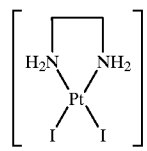

(c) reacting said compound with AgNO$_3$, the reaction being carried out in a suitable solvent, under suitable conditions so as to form a compound having the structure:

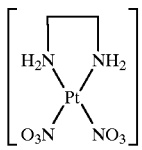

(d) reacting said compound with KCl in a suitable solvent under suitable conditions so as to form a compound having the structure:

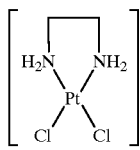

(e) reacting said compound with AgNO$_3$ in a suitable solvent, under suitable conditions so as to form a compound having the structure:

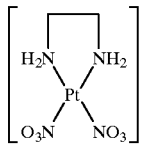

(f) recovering said compound as modified platinum starting compound for the synthesis of hapten-bound Pt(en) compounds for use as DNA and/or RNA label.

EXAMPLE 1

A. Preparation of Pt(en)-diamine Starting Material
Preparation of Platinumethylenediamine(NO$_3$)$_2$: Starting Material
Pt(en)(NO$_3$)$_2$
All Reactions are Performed in the Dark Dissolve 1 gram potassium tetrachloroplatinate (II), K$_2$PtCl$_4$ (2.4 mmol, Sigma) in 50 ml millipore (filtered water) and stir at room temperature. Add 10 equivalents of potassium iodide, KI (24 mmol, 3.999 g, Sigma). The colour of the solution will immediately turn from orange into dark red (K$_2$PtI$_4$), stir for 5 minutes.

Add one equivalent ethylenediamine (2.4 mmol, 160.8743 µl, Merck 11=0.9 kg) after diluting 161 µl ethylenediamine in 5 ml millipore very slowly to the platinum solution, mix this solution for 1 hour at room temperature. A yellow/brown precipitate, Pt(en)I$_2$, will be formed and the liquid standing above should be clear.

Filter the solution through a 1.0 µm membrane filter (Schleicher & Schuell), wash the precipitate with millipore, ethanol and diether (in this order). Dry the Pt(en)I$_2$ for at least 4 hours in a vacuum dryoven at 37° C.

Weigh the dried Pt(en)I$_2$ (~1.07 g) and suspend it in 45 ml millipore/5 ml acetone, the solution will be cloudy. Add 1.95 equivalent of AgNO$_3$ (M=169.9, Sigma). Stir the reaction overnight at room temperature.

Filter the solution through a 1.0 µm membrane filter, the precipitate is silver iodide, AgI, the filtrate should be clear.

Add to 0.5 ml of the filtrate, Pt(en)(NO$_3$)$_2$, an excess of KCl or NaCl and make sure that no white precipitate is formed immediately after adding the excess of KCl or NaCl. If no white precipitate (only a yellow one) is formed than add an excess of KCl or NaCl to the entire filtrate. After the yellow precipitate is formed filter the solution and wash the precipitate (Pt(en)Cl$_2$) with millipore, ethanol and diether.

Dry the precipitate for at least 4 hours in a vacuum dry oven at 37° C.

Weigh the dry Pt(en)Cl$_2$ (M=326,1), and suspend it in 45 ml millipore/5 ml acetone and stir the cloudy suspension. Add 1.95 equivalent AgNO$_3$ and stir the solution overnight at room temperature. The colour of the solution will become white, due to the formation of AgCl.

Filter the solution in the dark and evaporate the filtrate to remove the acetone by rotation evaporation until 25 ml of the filtrate is left. The filtrate is then freeze dried. The product is checked by NMR or Infrared Absorption Spectroscopy.

B. Preparation of Pt(tmen)-diamine Starting Material

Preparation of Platinum-N,N,N',N'-tetramethylethylenediamine(NO$_3$)$_2$: Starting Material Pt(tmen) (NO$_3$)$_2$
All Reactions are Performed in the Dark Repeat the entire procedure of Example 1A, but use N,N,N',N'-tetramethylethylenediamine instead of ethylenediamine.

EXAMPLE 2

A. Preparation of [Pt(en)(BioDadoo-NH$_2$)(NO$_3$)](NO$_3$)

Dissolve Pt(en)(NO$_3$)$_2$ (18.2 mg, 0.048 mmol) in 10 ml of Millipore water and heat until dissolving. Dissolve BioDadoo (20 mg, 0.053 mmol, purchased from Boehringer Mannheim) in 5 ml of Millipore water. Add the two solutions together and adjust the pH to 8 by 0.1 N NaOH, react for at least 3 hours at 50° C. Isolate the end product by freeze drying.

B. Preparation of [Pt(tmen)(BioDadoo-NH$_2$) (NO$_3$)](NO$_3$)

Dissolve Pt(tmen)(NO$_3$)$_2$ (35 mg, 0.08 mmol) in 12.5 ml of Millipore water and heat until dissolving. Dissolve BioDadoo (32 mg, 0.085 mmol) in 10 ml of Millipore water. Add the two solutions together and adjust the pH by 0.1 N NaOH, react for at least 4 hours at 50° C. Isolate the end product by freeze drying.

C. Preparation of [Pt(en)(DigDadoo-NH$_2$)(NO$_3$)](NO$_3$)

Dissolve Pt(en)(NO$_3$)$_2$ (5 mg, 0.013 mmol) in 5 ml of Millipore water and heat until dissolving. Dissolve DigDadoo (9 mg, 0.016 mmol, purchased from Boehringer Mannheim) in 5 ml of Millipore water. Add the two solutions together and react for at least 4 hours at 50° C. Isolate the end product by freeze drying.

EXAMPLE 3

A. Preparation of a Labeled dGTP

Dissolve [Pt(en)(BioDadoo-NH$_2$)(NO$_3$)](NO$_3$) (9 mg, 0.012 mmol) in 2 ml of Millipore water. Add 2'-deoxyguanosine-5'-triphosphate (2.3 mg, 0.004 mmol) and adjust the pH to 6. Incubate for 24 hours at 50° C., freeze-dry and redissolve in Millipore water (1 ml) and filter through a membrane filter. Apply the mixture to a FPLC with MonoQ and purify with a linear gradient from 100% Millipore water to 100% 1M NH$_4$HCO$_3$, collect and pool appropriate fraction and isolate by freeze drying. Dissolve the product in a 100 mM solution of triethylamine ammonium acetate (TEAA) (1 ml) and apply to a Reversed Phase HPLC (C18) with a linear gradient from 100% 100 mM TEAA to 50% 100 mM TEAA/50% 100 mM TEAA/acetonitrile (1/1 v/v), collect and pool the appropriate fraction and remove solvents by repeated evaporation in vacuo. Pass the product over a cation exchanger (Dowex) in the lithium form, isolate the product by freeze drying.

B. Preparation of a Labeled 5-AA-dUTP

Dissolve [Pt(en)(BioDadoo-$NH_2$)($NO_3$)]($NO_3$) (6 mg, 0.008 mmol) in 2 ml of Millipore water. Add 2'-deoxyuridine-5-aminoallyl-51'-triphosphate (2 mg, 0.004 mmol) and adjust the pH to 8. Incubate for 24 hours at 50° C., freeze-dry and redissolve in Millipore water (1 ml) and filter through a membrane filter. Apply the mixture to a FPLC with MonoQ and purify with a linear gradient from 100% Millipore water to 100% 1M $NH_4HCO_3$, collect and pool appropriate fraction and isolate by freeze drying. Dissolve the product in a 100 mM solution of triethylamine ammonium acetate (TEAA) (1 ml) and apply to a Reversed Phase HPLC (C18) with a linear gradient from 100% 100 mM TEAA to 50% 100 mM TEAA/50% 100 mM TEAA/acetonitrile (1/1 v/v), collect and pool the appropriate fraction and remove solvents by repeated evaporation in vacuo. Pass the product over a cation exchanger (Dowex) in the lithium form, isolate the product by freeze drying.

EXAMPLE 4

Reaction for Coupling Pt(en)-compounds to DNA

Typical Reaction for Labeling DNA Molecules with a Pt-Compound According to the Invention 5 µg of double stranded DNA is sonicated or DNase treated to yield fragments of 300–500 bp. 6 µg of Pt(en)-compound is added and the volume is adjusted to 50 µl with demineralised water. The reaction mixture is incubated at 65° C. for 1 hour. Non-bound Pt(en)-compound is blocked by adding 100 µl of a NADDTC solution. The Pt(en)-compound labeled DNA is purified on a sephadex G-50 column. Readily labeled and purified DNA is stored at –20° C. or used directly in a DNA probe based assay. Pt(en)-compound labeled DNA probes can be stored at least 2 years at –20° C. without loss of activity and/or specificity. All applications mentioned are carried out with probes labeled according to this protocol.

EXAMPLE 5

Biotin Labeling of DNA Probes with [Pt(en)(BioDadoo-$NH_2$) ($NO_3$)]($NO_3$)(BioDadoo-ULS)

Introduction

The labeling method has been used to label DNA probes with Biotin for In Situ Hybridization (ISH). In this example labeling procedures including the protocols and data for quality control procedures are presented. For Biotin labeling a plasmid cloned total DNA of Human Papilloma Virus type 6 (HPV-6, 40% GC basepairs) was used.

Experimental Procedures

Plasmid DNA Preparation

Total DNA of Human Papilloma Virus type 6 was cloned into vector pSp-64. Plasmid DNA was transferred into *E. coli* (C-600) and plated onto ampicillin containing LB plates Single colonies were grown overnight in large culture. Plasmid DNA was isolated according to the method of Birnboim and Doly[1], purified by Sepharose Cl-2B columnchromatography (Pharmacia) and checked for inserts by restriction-enzyme-analyses. Plasmid DNA concentration was determined by A260/280 absorbtion. After ethanol precipitation the DNA was reconstituted in 10 mM TRIS/HCl pH 7.2, 0.3 mM EDTA to a final concentration of 1 µg/µl (batch# 150894). Subsequently this DNA was sonicated (Soniprep 150., MSE) for 3 times 10 minutes (amplitude 5 microns) on ice.

The size of the resulting DNA fragments was determined by 2% agarose gel electrophoresis and found to be in between 200–400 basepairs (batch# 051094).

Plasmid DNA Labeling and Purification

Plasmid HPV-6 DNA was labeled with BioDadoo-ULS by mixing the following reagents:

| | |
|---|---|
| plasmid HPV-6 DNA (batch# 051094) | 5 µl (1 µg/µl) |
| BioDadoo-ULS labeling reagent (batch# BX940830) | 8 µl (1 µg/µl) |
| Demineralised water (<0.2/ µS/cm) | 37 µl |

The 50 µl reaction mixture was incubated for 15 minutes at 85° C.

Excess of labeling reagent was captured by adding 50 µl sodium diethyldithiocarbamate (2% solution in demineralised water) and incubating for 30 minutes at room temperature. Unbound BioDadoo-ULS was removed, using a S300 HR microspin column (Pharmacia), by size exclusion chromatography. Eluent volume was adapted to 500 µl giving a 10 ng/µl biotin HPV-6 probe concentration (batch# 061094).

Quality Control for Detection Limits

The detection limit of the biotin probe of the invention was determined by direct spot blot and reversed filterhybridization according to the following protocols:

Direct Spot Blot

HPV-6 probe (batch# 061094) labeled with biotin according to the invention was 10-fold serially diluted into spot buffer comprising 900 mM sodium chloride, 90 mM sodium citrate and 200 µg/ml single stranded salmon sperm DNA giving a dilution series varying from 1000–0.1 pg biotin probe per µl. 1 µl spots were applied onto nitrocellulose membrane and incubated for 2 hours at 80° C. to blind the DNA. The biotin probe was visualized using a streptavidin-alkaline phosphatase conjugate (Sigma) combined with a NBT/BCIP precipitating substrate solution (Sigma) according to the following protocol:

Membranes were soaked in TBS solution containing 0.5% TWEEN20 (TBST) for 5 minutes Membranes were incubated with Strep-AP (3 DEA U/ml) in TBST for 15 minutes at 37° C.

NC-membranes were washed 3 times 5 minutes in TBS solution followed by a 5 minute wash step in demineralised water.

Membranes were incubated with NBT/BCIP substrate solution for 15 minutes at 37° C., subsequently washed in demineralised water and air dried.

Results

By using this method the detection limit of the biotin DNA probe according to the invention was found to be less than 1 pg.

Reversed Filter Hybridization

HPV-6 DNA (batch# 051094) was1 in 10 diluted in 0.1N NaOH, incubated at 100° C. for 5 minutes and directly placed on ice for 5 minutes to make DNA single stranded.

A 10-fold serial dilution was made in cold 0.1N NaOH to give a series varying from 10,000–1 pg DNA per µl. 1 µl spots were applied onto Nylon membrane (Boehringer Mannheim) and air dried.

HPV-6 DNA probe that was labeled with biotin according to the invention was diluted in 5×SSPE 0.5% SDS solution to yield a concentration of 200 ng/ml.

This solution was incubated for 5 minutes at 100° C. and placed directly on ice for 5 minutes.

Nylon membranes containing target DNA were soaked in 2×SSC for 5 minutes and subsequently incubated with the single stranded probe solution for 2 hours at 37° C.

Excess of the biotin probe was removed by three changes in 2×SSPE 0.1% SDS for 10 minutes at 37° C. followed by a 5 minutes TBST incubation.

The biotin probe of the invention was visualized by performing the same protocol as described in the direct spot blot method.

Results

By using this procedure the detection limit of the biotin probe according to the invention was found to be less than 10 pg.

Performance in In Situ Hybridization

The test material consisted of 6 µm paraffin sections of a HPV-6 posotive cervical condyloma mounted on organosilane coated glass slides.

The following protocol was applied (unless otherwise stated steps are at room temperature):

1 Paraffin sections were dewaxed in 3 changes of xylene and hydrated in graded ethanol.
2 Sections were rinsed in TBST for 5 minutes.
3 Sections were digested in 0.25% pepsin in 0.1N HCl for 30 minutes at 37° C., dehydrated in graded ethanol and air dried.
4 µl of probe solution was applied to a section and covered with a coverslip.

Probe solution consisted of biotin HPV-6 probe DNA labeled according to the invention (batch# 061094) in a concentration of 2 ng/µl dissolved in hybridization mixture comprising 0.6M NaCl, 0.06M sodium citrate, 35% formamid, 10% dextransulphate, 2,5× Denhardts and 10 µg/ml single stranded salmon sperm DNA.

5 Slides were placed on a hot plate set at 95° C. for 5 minutes to denature probe and target DNA simultaneously.
6 Hybridization was performed by placing the slides in a humidified chamber at 37° C. for 2 hours.
7 Coverslips were removed and slides were washed in 3 changes of 15 mM NaCl, 1.5 mM sodium citrate and 5% formamid for 10 minutes at 37° C.
8 Slides were rinsed in TBST.
9 Sections were incubated with Streptavidin AP conjugate (3DEA U/ml in TBST) for 15 minutes at 37° C.
10 Slides were washed in TBST (3×) and demineralised water (1×) for 5 minutes.
11 Sections were incubated with NBT/BCIP substrated solution for 15 minutes at 37° C.
12 Slides were washed in demineralised water (3×) for 1 minute and sections were mounted in glycerol/gelatin.

Results

By using the sections showed blue/purple precipitates at the sites of HPV-6 infected cells and minor background in the remaining tissue.

Conclusions

The results demonstrate that DNA labeled according to the invention has good detection limits. The present method is very well suited for research, routine and for industrial production of labeled nucleic acids, as the method is fast and easy to perform, very sensitive, and does not include any enzymatic step, which makes it highly reproducible and fitted for an overall low cost production. The method of the invention offers a useful alternative equaling conventional non-isotopic labeling methods.

GENERAL REFERENCES

1. Maniatis T., Sambrook J., Fritsch E. F., Molecular Cloning, Second Edition, Cold Spring Harbor Laboratory Press, ISBN 0-8769-309-6.
2. Keller G. H., Manak M. M., DNA probes, Stockton Press, ISBN 0-333-47659-X.

Applications

1. The Use of Pt-DNA Linkers of the Invention in the So Called LIDIA Technique: Linked DNA Immuno Assay The LIDIA technique enables the quantitative analysis of small amounts of DNA (or RNA) e.g. after a PCR amplification of the starting material. The technique is sensitive and specific, due to the use of specific DNA(RNA) probes in accordance with the invention and easy to perform, because of the quick DNA(RNA) Pt-labeling steps of the invention.

Description of the Technique

The technique uses fast Pt labeling compounds of the invention to label DNA(RNA) probes This technique is possible with 3 different approaches.

1. Linking DNA probes molecules to a surface by using a Pt compound in accordance with the invention which cross-link DNA molecules irreversibly to plastic, nylon or nitrocellulose. Detection of DNA targets can then be accomplished by using classically labeled DNA/RNA probes.(nick translation or chemical modification, random priming)
2. Linking a detectable group to the DNA, to render a DNA molecule into a so-called DNA probe. Binding of DNA compounds to a surface can then be accomplished by using classic techniques known to science (covalent linking to specially treated microtiter plates, baking of DNA molecules onto nitrocellulose or binding of DNA molecules to nylon membranes.
3. A combination of techniques 1 and 2

Approach 1

An immobilized DNA probe can be used to catch specific target molecules in a sample by using a hybridization technique. Detection of formed hybrids can be done by using different techniques, e.g. a second labeled DNA probe can be used to hybridize with a different site on the target DNA molecule to form a sandwich hybrid. The label can then be detected by using state of the art immunological detection and colouring techniques.

Approach 2

A volume containing (amplified) detectable DNA(RNA) is directly labeled according to the protocol in accordance with the invention.

Excess label is quenched by adding NaDDTC or Thioureum. This approach distinguishes itself from other techniques by the fact that the target molecule is labeled in contrast to other assay were labeled DNA(RNA) probes are used to detect the target. The quick binding capacity of the Pt-label compound of the invention enables a DNA binding step as a routine step in a diagnostic test procedure (normal binding times are 60 minutes at 65° C.).

A second step is performed in a microtiter plate precoated with a target specific probe. Incubation is allowed to the formation of stable "Labelled target" and probe hybrids. The direct labeling of target molecules enables the omission of laborious double hybridization techniques where one probe is used to catch the target and another labeled probe is used to detect the immobilized target.

In this method the probes are covalently linked to the microtiter plate to the surface of the wells. The second incubation step has the character of a liquid hybridisation and therefore can be performed very rapidly. This is one of the main innovative features of this approach to quantitive DNA hybridisation techniques.

Approach 3

Both for the immobilization of DNA probes or DNA targets and for the labeling of DNA probes and targets the newly developed Pt system can be used. These two DNA linking techniques can be combined into one assay where both the "catcher" and the "detector" are linked to a second substance (either a detectable group like biotin, digoxigenin or a carrier surface like a plastic stick, microtiter plate or a membrane).

Examples of the technique: the detection of STD related microorganisms in human diagnostics (Chlamydia, Syfilis, AIDS, Herpes, Gonorrhoea, Hep. B,)

2. The Use of Pt-DNA Labels of the Invention in Combination with Test Strip Procedures and Formats the "DNA Dipstick".

The DNA dipstick technique enables the qualitative and semi-quantitative analysis of small amounts of DNA(or RNA) e.g. after a PCR amplification or freely present in samples of body fluids (blood, urine, sweat etc.)

The technique is sensitive and specific, due to the use of specific DNA(RNA) probes and easy to perform because of the quick DNA(RNA) Pt-labeling steps according to the invention.

The universal labeling characteristics of the newly developed Pt label can be used in 3 ways to achieve a bound DNA(RNA) molecule.
1. It can be used to attach a detectable marker group to a polynucleotide sequence.
2. It can be used to attach polynucleotide sequences irreversibly to a solid phase (plastic, membranes, latex beads, hydrosols or microtiter plate wells).
3. A combination of 1 and 2 ad 1

In this example there is a twofold approach to the detection of biolytes biological analytes in test samples. Firstly a DNA probe can be labeled with the newly developed Pt labeling compound. This labeled probe can then be used to detect preformed hybrids on a membrane formed between the target DNA sequence and a primary probe. It is essential in this method that the primary probe recognizes a different sequence on the target than the secondary Pt labeled probe. In practice, this can be achieved for instance with RNA hybridization where a POLY T probe is used as a primary probe to immobilize all RNA (recognizable by its POLY A tails) to a membrane.

The second approach differs slightly in that in this case the target can be labeled in the test sample fluid, because of the fast and very specific Pt labeling characteristics. A procedure like this would comprise a catch of the labeled target with an immobilized specific unlabeled DNA probe on a suitable membrane. Hence a dipstick version for DNA/RNA applications.

ad 2

To immobilize DNA probes or target DNA, a non-labeled Pt compound (that is a Pt compound with 2 free binding sites) can be used to act as a bridge between DNA and the surface of carriers (plastic, membrane, microtiter plates etc.)

It greatly enhances the usability of DNA sequences as catcher molecules in diagnostic assays, since there are little substances known to science that bind readily DNA in a spontaneous way. Introducing this Pt bridge molecule a wide field of new applications for the DNA technology has come within reach.

ad 3: a Combination of Example 1 and 2

General: the use of the Pt compound of the invention in latex or hydrosol assays is particularly interesting. The compound enables the coupling of DNA molecules to small particles. The DNA molecules can be hybridized to target material. A positive reaction is visualized by an agglutination of the particles, due to crosslinking of the DNA hybrid particle compounds.

A test like this can be made quantative, the rate of agglutination can be tuned and measured at a specific wavelength. Especially gold particles have the intrinsic characteristic that a shift in optimal wavelength occurs after agglutination.

3. Detection of Platinated DNA Probes of the Invention with the the Silver-enhancement Technique Platinated DNA/RNA probe can be employed in hybridisation methods to detect DNA/RNA sequences in sample material. The introduction of a platinum compound at the site of the target enables the deposition of Ag molecules in a chemical reaction especially designed to reduce ionic silver to metallic silver. At the site of a Pt nucleus a decomposition of metallic silver(black) occurs due to the catalytic effect of the Pt nucleus.

Ionic silver is reduced by a reducing agent (e.g. Na-borohydrid, Hydrochinon) in solution. In a constant ratio the amount of silver deposited on the Pt is proportional to the length of the enhancement incubation. Visualisation of a non-visible Pt nucleus can be accomplished by the empirical observation of the appearace of a black spot in the test sample.

The black spots indicate the site of specific probes binding and thus the site of specific target location. The technique enables a quick and easy diagnostic procedure for the detection of various microorganisms and gene translocations/abnormalities.

What is claimed is:

1. A method for labeling a nucleotide comprising:
   providing a label;
   providing a spacer means comprising a spacer reactive moiety at one end and an electron donating moiety at the other end of the spacer means, wherein the spacer reactive moiety is capable of coupling the spacer means to a label when the spacer reactive moiety is reacted with the label;
   providing a nucleotide;
   providing a linker having formula I,

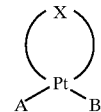

(I)

wherein X represents an aliphatic diamine, and A and B represent the same or different linker reactive moieties capable of reacting with the electron donating group of the spacer means or with the nucleotide, thereby attaching the spacer means or the nucleotide to the linker;
   reacting the spacer reactive moiety with the label, thereby coupling the spacer means to the label;
   reacting the electron donating moiety of the spacer means with one of the linker reactive moieties, thereby attaching the spacer means to the linker; and
   reacting the nucleotide with the other linker reactive moiety, thereby attaching the nucleotide to the linker.

2. The method according to claim 1, wherein X represents an aliphatic diamine having 2–6 carbon atoms.

3. The method according to claim 1, wherein X represents an aliphatic diamine having the formula $G_2NCH_2CH_2NG_2$, wherein G represents H or an alkyl group of from 1 to 6 carbon atoms.

4. The method according to claim 1, wherein X represents ethylenediamine.

5. The method according to claim 1, wherein X represents N,N,N',N'-tetramethylethylenediamine.

6. The method according to claim 1, wherein A and B represent $NO_3^-$, $SO_3^-$, $Cl^-$, $I^-$, other halogen or $Me_2SO$.

7. The method according to claim 1, wherein A and B are the same.

8. The method according to claim 1, wherein the spacer means comprises no more than twenty carbon atoms.

9. The method according to claim 8, wherein the carbon atoms are non-branched.

10. The method according to claim 1, wherein the spacer means comprises four carbon atoms and one heteroatom.

11. The method according to claim 1, wherein the heteroatom is oxygen.

12. The method according to claim 1, wherein the spacer means is 1,8-diamino-3,6-dioxaoctane.

13. The method according to clam 1, wherein the spacer means is an oligolysine or a polylysine.

14. The method according to claim 1, wherein the electron donating moiety is an amino group or a thiolate group.

15. The method according to claim 14, wherein the amino group is an aromatic amino group.

16. The method according to claim 14, wherein the amino group is an imidazole or purine group.

17. The method according to claim 1, wherein the spacer reactive moiety is $NH_2$.

18. The method according to claim 1, wherein the label is radioactive.

19. The method according to claim 1, wherein the label is an enzyme.

20. The method according to claim 1, wherein the label is a component of a specific binding pair.

21. The method according to claim 1, wherein the specific binding pair is biotin and avidin or streptavidin.

22. The method according to claim 1, wherein the label is a dye, a fluorochrome, or a reducing agent.

23. The method according to claim 1, wherein the label is digoxygenin.

24. The method according to claim 1, wherein the nucleotide is adenine, thymidine, cytosine, and either guanine or uridine.

25. The method according to claim 1, wherein the nucleotide is a purine.

26. The method according to claim 1 wherein the linker is reacted with a labeling moiety comprising moiety comprising (II)

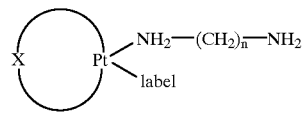

or the formula (III)

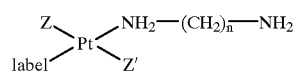

wherein X represents an aliphatic diamine, Z and Z' represent a non-leaving ligand and n is an integer of from 2 to 10.

27. A method according to claim 26, wherein Z and/or Z' represent an $NH_3$, $NH_2R$, $NHR_2$, or $NR_3$ group, wherein R represents an alkyl group having from 1 to 6 carbon atoms.

28. A method according to claim 1, wherein the nucleotide is a constituent of a DNA or RNA polynucleotide.

* * * * *